US007896849B2

(12) United States Patent
Delay

(10) Patent No.: US 7,896,849 B2
(45) Date of Patent: Mar. 1, 2011

(54) SYRINGE FOR MEDICAL INTERVENTIONS AND KIT FOR RECONSTITUTING EXTEMPORANEOUS SUBSTANCES

(75) Inventor: Jean-Pascal Delay, Ecully (FR)

(73) Assignee: SEDAT, Irigny (FR)

( * ) Notice: Subject to any disclaimer, the term of this patent is extended or adjusted under 35 U.S.C. 154(b) by 498 days.

(21) Appl. No.: 11/568,561

(22) PCT Filed: Apr. 27, 2005

(86) PCT No.: PCT/FR2005/001046
§ 371 (c)(1),
(2), (4) Date: Nov. 1, 2006

(87) PCT Pub. No.: WO2005/120431
PCT Pub. Date: Dec. 22, 2005

(65) Prior Publication Data

US 2008/0009790 A1 Jan. 10, 2008

(30) Foreign Application Priority Data

May 3, 2004 (FR) ..................................... 04 04717

(51) Int. Cl.
*A61M 5/00* (2006.01)

(52) U.S. Cl. ......... 604/181; 604/187; 604/128; 604/131; 604/138; 604/226; 604/82; 600/579; 600/583

(58) Field of Classification Search .......... 604/128–231, 604/82–92; 600/579, 583
See application file for complete search history.

(56) References Cited

U.S. PATENT DOCUMENTS

| | | | | | |
|---|---|---|---|---|---|
| 3,511,239 | A | * | 5/1970 | Tuschhoff | 604/89 |
| 3,626,928 | A | * | 12/1971 | Barringer et al. | 600/563 |
| 3,957,052 | A | * | 5/1976 | Topham | 604/236 |
| 4,206,768 | A | * | 6/1980 | Bailey | 600/576 |
| 4,237,880 | A | * | 12/1980 | Genese | 604/81 |
| 4,447,235 | A | * | 5/1984 | Clarke | 604/167.02 |
| 4,532,969 | A | | 8/1985 | Kwaan | |
| 4,640,297 | A | * | 2/1987 | Bates | 600/578 |
| 4,824,434 | A | * | 4/1989 | Seitz, Jr. | 604/27 |
| 4,900,322 | A | * | 2/1990 | Adams | 604/410 |
| 4,941,883 | A | * | 7/1990 | Venturini | 604/186 |
| 5,042,979 | A | * | 8/1991 | Anderson et al. | 604/319 |
| 5,078,864 | A | * | 1/1992 | Whittier | 210/137 |
| 5,286,257 | A | * | 2/1994 | Fischer | 604/82 |

(Continued)

FOREIGN PATENT DOCUMENTS

EP 521 460 1/1993

*Primary Examiner* — Nicholas D Lucchesi
*Assistant Examiner* — Scott Medway
(74) *Attorney, Agent, or Firm* — Sughrue Mion, PLLC

(57) ABSTRACT

A syringe (12) having: a syringe body (18) in which a passage (28) for the circulation of fluid is defined, the circulatory passage (28) being extended by a main element (20) for fluidic connection to a complementary volume (13); and a movable piston (36) inside the syringe body (18), defining, with the syringe body (18), a chamber for the containment of fluid, opening out through the circulatory passage (28). The syringe body (18) defines a closed space in which the piston (36) is movably mounted. The piston (36) also defines in the closed space an auxiliary return chamber. The syringe body (18) defines a return passage (48) opening out into the auxiliary return chamber (46). The return passage (48) is extended by an auxiliary element (50) for connection to the complementary volume (13).

10 Claims, 6 Drawing Sheets

U.S. PATENT DOCUMENTS

Figure 1:
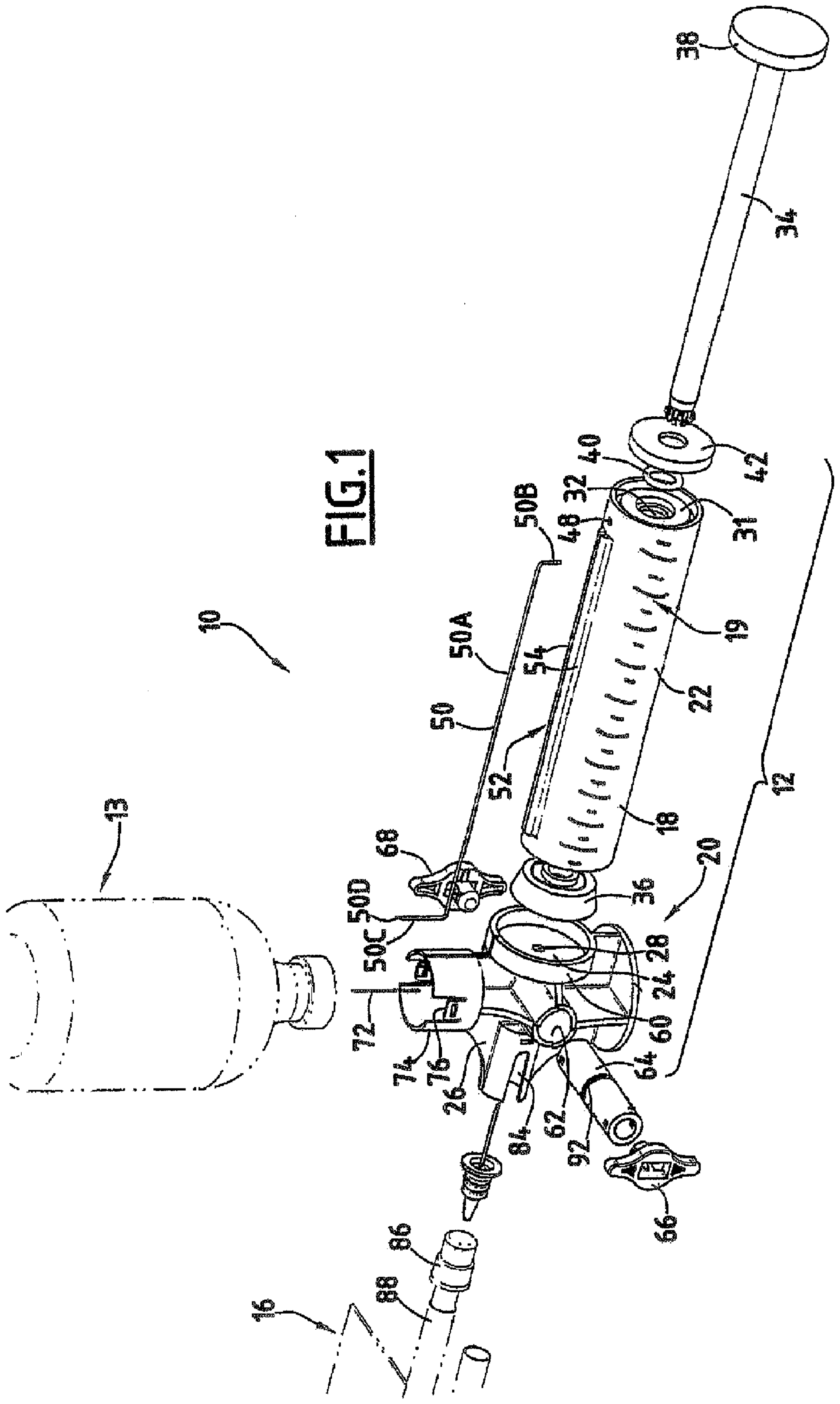

| | | | | | |
|---|---|---|---|---|---|
| 5,360,410 | A | * | 11/1994 | Wacks | 604/232 |
| 5,433,705 | A | * | 7/1995 | Giebel et al. | 604/82 |
| 5,466,220 | A | * | 11/1995 | Brenneman | 604/87 |
| 5,564,629 | A | * | 10/1996 | Weissman et al. | 239/8 |
| 5,643,218 | A | | 7/1997 | Larkin et al. | |
| 6,050,957 | A | * | 4/2000 | Desch | 600/579 |
| 6,238,372 | B1 | * | 5/2001 | Zinger et al. | 604/246 |
| 6,558,537 | B1 | * | 5/2003 | Herrington et al. | 210/192 |
| 6,730,046 | B1 | * | 5/2004 | Hamamoto et al. | 600/583 |
| 6,981,963 | B2 | * | 1/2006 | Barker et al. | 604/90 |
| 7,455,658 | B2 | * | 11/2008 | Wang | 604/85 |
| 2004/0236273 | A1 | * | 11/2004 | Tanaka et al. | 604/89 |

* cited by examiner

SYRINGE FOR MEDICAL INTERVENTIONS AND KIT FOR RECONSTITUTING EXTEMPORANEOUS SUBSTANCES

The present invention concerns a syringe and a kit for reconstituting extemporaneous substances, comprising said syringe.

The invention concerns in particular a syringe of the type comprising:

a syringe body in which a passage for the circulation of fluid is defined, said circulatory passage being extended by a main element for fluidic connection to a complementary volume, and a movable piston inside the body of the syringe defining, with the syringe body, a chamber for the containment of fluid, which containment chamber opens out through said circulatory passage.

In the medical field, it is known to use a syringe for effecting the reconstitution of an extemporaneous mixture constituted by a solvent and a cytotoxic active ingredient. The active ingredient is for example used for the treatment by chemotherapy of patients affected by cancer.

As is known per se, the solvent is commonly contained initially in a perfusion bag, while the cytotoxic active ingredient, generally in powder form, is initially contained in a bottle. For the preparation of the extemporaneous mixture, the practitioner removes solvent from the bag in order to introduce it into the body of a syringe. The solvent thus removed is introduced into the bottle, where it mixes with the powder constituting the active ingredient. The mixture thus reconstituted is re-aspirated into the syringe, before being transferred back into the perfusion bag. This is then placed on a perfusion line for gradually administering its contents to the patient.

During the successive transfers, the excess air contained in the bottle, at the time of introduction of the solvent, is evacuated into the atmosphere through a vent provided for this purpose. The solvent vapours, and especially the gaseous emanations resulting from the active ingredient, escape through said vent. They may be dangerous for the medical staff carrying out the transfer. Thus, it is known to equip the vent with a filter having openings of 0.2 μm in order to retain the harmful molecules in the bottle.

However, the actual efficacy of such a filter is questionable and the utilisation of said filter is delicate and expensive.

The aim of the invention is therefore to propose a syringe avoiding such gaseous emissions which may be harmful to the medical staff.

To this end, the subject of the invention is a syringe of the aforesaid type, characterized in that the syringe body defines a closed space in which the piston is movably mounted, the piston defining in this closed space, in addition to the fluid containment chamber, an auxiliary return chamber, the syringe body defining a return passage opening out into said auxiliary return chamber, and in that said return passage is extended by an auxiliary element for connection to said complementary volume. According to particular embodiments, the syringe includes one or more of the following characteristics:

said auxiliary connection element comprises a hollow needle;

it comprises a piston actuating rod linked to the piston and protruding out of the syringe body from a rearward end, said circulatory passage being formed at the forward end of the syringe body, and said return passage is formed in the vicinity of the rearward end of the syringe body and the auxiliary connection element extends along the length of the syringe body from the return passage to the vicinity of the forward end;

the main element for fluidic connection includes a distributor comprising a base defining at least three paths for circulation and a closure means, movable in relation to the base, a first path being connected to said circulatory passage, a second path comprising a duct for connection to said complementary volume, and a third path comprising a transfer duct, said closure means being movable between a transfer position, in which the first and third paths are connected, and a preparation position, in which the first and second paths are connected.

the syringe body and the distributor are inseparable;

the transfer duct comprises a hollow needle; and said hollow needle of the transfer duct has a perforable and resiliently deformable hood covering the hollow needle;

the connecting duct comprises a hollow needle;

the free end portions of the hollow needles of the auxiliary connection element and of the connecting duct are spaced by less than 1 cm.

A further subject of the invention is a reconstitution kit comprising a syringe as defined above and a complementary volume adapted for simultaneous connection to the containment chamber and to the auxiliary return chamber respectively via the main element for fluidic connection and the auxiliary connection element.

The invention will be understood more clearly on reading the following description, provided solely by way of example and with reference to the drawings, in which:

FIG. 1 is an exploded perspective view of a reconstitution kit including a syringe according to the invention; and FIGS. 2 to 6 are views in longitudinal section of the kit at successive stages of use.

The reconstitution kit 10 illustrated in FIG. 1 is intended in particular for the extemporaneous preparation of a cytotoxic or other drug for the treatment of cancers or the like by chemotherapy.

Figure 4:
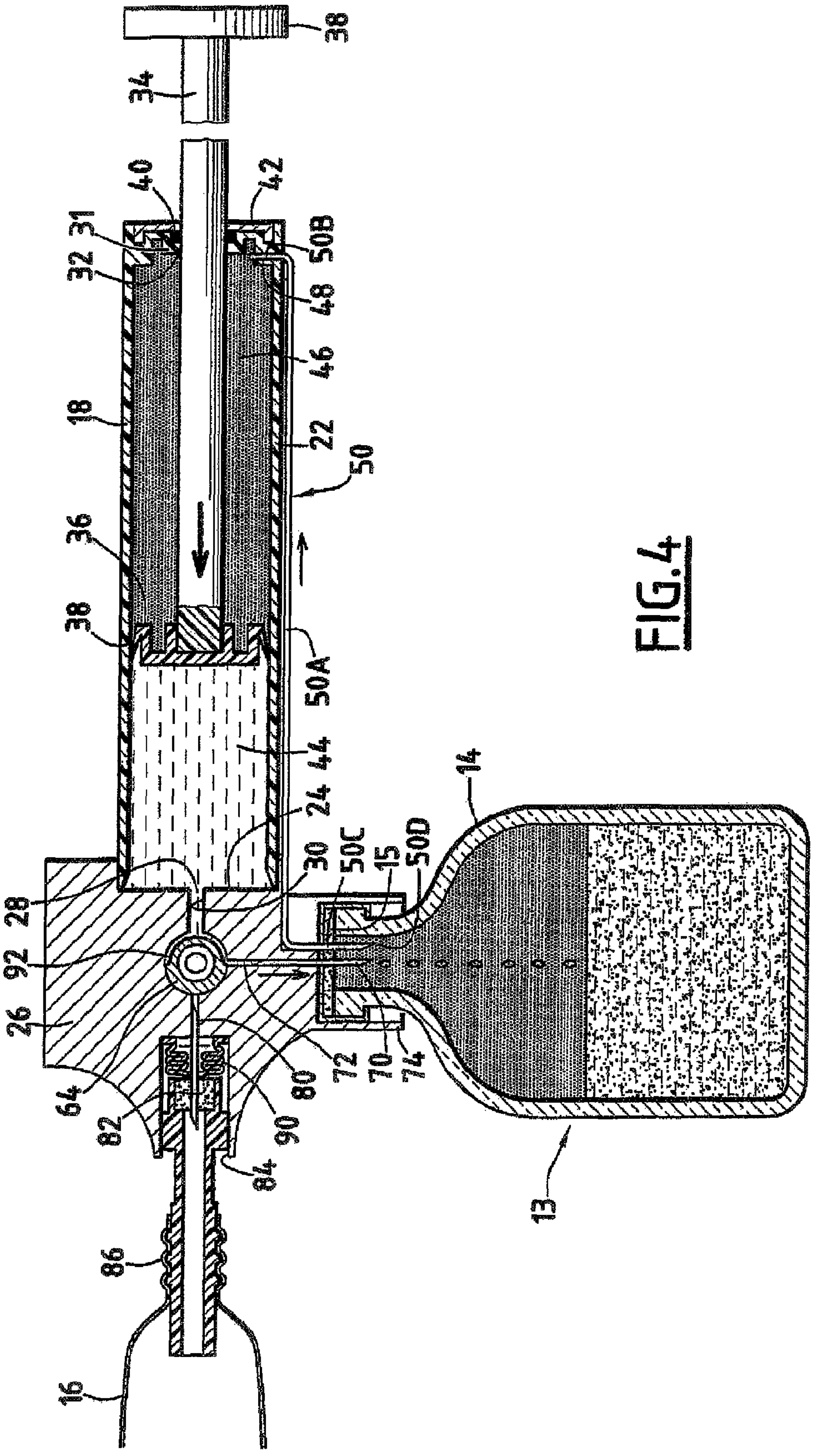

The kit basically includes a syringe 12 and a bottle initially containing an active ingredient in powder form. The bottle 13 is formed, for example and as illustrated in FIG. 4, of a body 14 of non-deformable glass closed by a protective cap 15, the body defining a closed space. It is initially filled with an active ingredient in powder or liquid form. The syringe 12 is suitable for being connected on the one hand to the bottle 13 and on the other hand to a perfusion bag 16.

More precisely, the syringe 12 comprises a syringe body 18 bearing graduations 19 and a three-way distributor 20 permitting the selective connection of a chamber of the syringe body selectively to the bottle 13 or to the perfusion bag 16.

As illustrated in FIGS. 2 to 6, the syringe body 18 comprises a cylindrical wall 22 of generally circular section closed, at a forward end, by a transverse wall 24 defined by a base 26 of the distributor 20. The wall 24 is pierced by a passage 28 for circulation of a fluid entering or leaving the syringe.

The passage 28 is extended by a duct 30 forming a first path of the distributor 20. At the rearward end of the syringe body 18, the cylindrical wall 22 is closed by a transverse wall 31 pierced in its centre by an opening 32 for the circulation of a piston rod 34.

The piston rod 34 is disposed along the axis of the syringe body and has at its end received in the syringe body a piston 36 displaceable axially from one end to the other of the syringe body, and having a peripheral lip 38 providing a seal along the wall. At its end protruding from the syringe body, the piston rod 34 has a transverse bearing surface 38. A sealing O-ring 40 is arranged against the transverse wall 31 at the periphery of the piston rod 34. The seal is compressed by a bearing washer 42.

Thus, the piston 36 defines in the syringe body, at the front, a fluid containment chamber 44. This chamber is generally closed and opens only through the circulatory passage 28. On the other side of the piston 36 an auxiliary return chamber 46 for gaseous excess is defined. The chambers 44 and 46 are complementary and together form a closed space defined by the syringe body 18.

The auxiliary return chamber 46 is closed and opens only through a return passage 48 for gaseous excess. This passage is extended by an auxiliary element 50 for connection to the bottle 13.

The auxiliary connection element 50 is formed of a metal or plastics tube of reduced section, for example of 0.5 mm inside diameter. The latter includes a straight main portion 50A and two elbowed end portions 50B, 50C extend generally perpendicularly to the straight main portion 50A.

The straight portion 50A has a length very slightly greater than the length of the syringe body 18. The rearward elbowed end 50B is engaged in the return passage 48.

The straight main portion 50A extends along the length of the cylindrical wall 22. For holding the tube 50, the syringe body has on its outer surface a channel 52 defined by two longitudinal lips 54 visible in FIG. 1.

The curved forward end 50C is bevelled at its end marked 50D, so that the auxiliary connection element 50 constitutes a hollow needle. The bevelled end 50D is suitable for engaging through the perforable protective cap 15 closing the neck of the bottle 13.

The base 26 of the distributor 20 is formed for example of injection-moulded plastics material.

The wall 24 forming the end of the syringe body is bordered externally by a collar 60 permitting the rigid connection of the cylindrical wall 22. This rigid connection is effected inseparably, for example by adhesive securing or ultrasonic welding, so that the distributor cannot be separated from the syringe body 18.

The base 26 defines a cylindrical seat 62 in which a sliding tap 64 of the distributor is received. The tap passes through the base from side to side and is equipped at each end with an operating member 66, 68.

Figure 2:
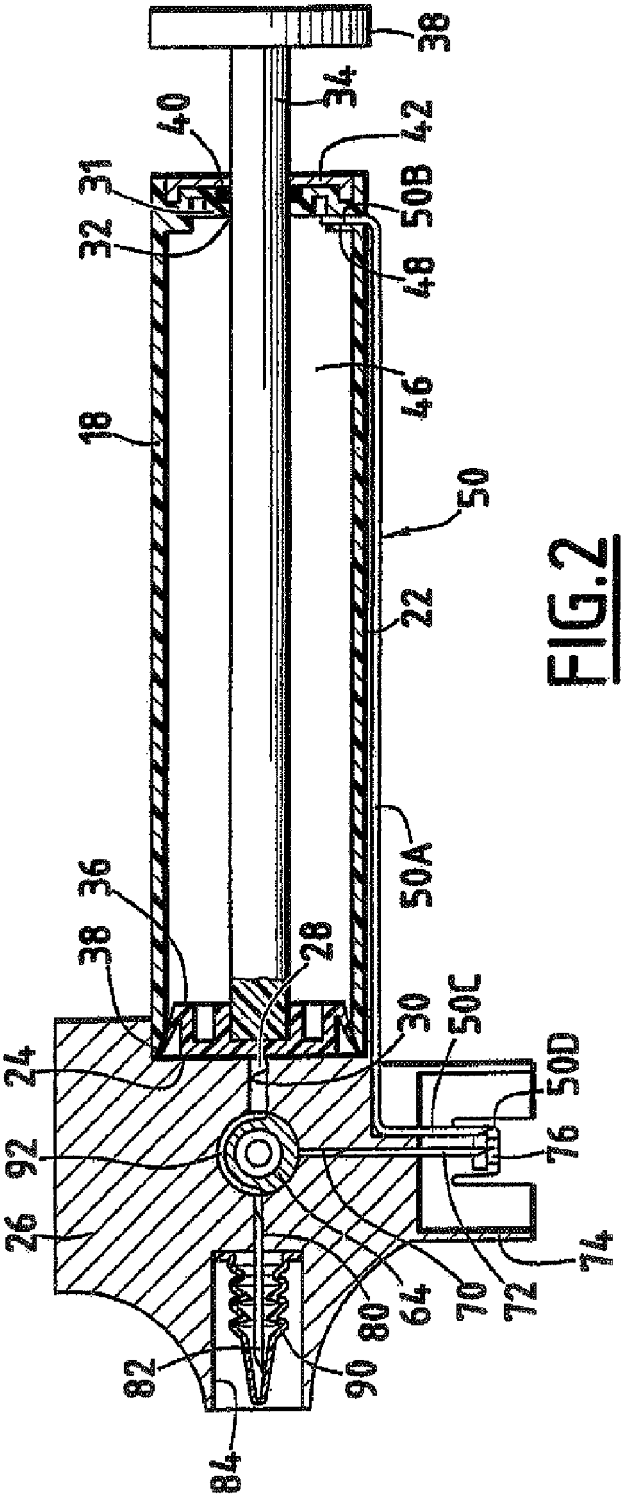

Besides the duct 30, two other ducts of the distributor open out into the seat 62. The three ducts of the distributor extend in the same plane and are offset by an angle of 90°, as illustrated in FIG. 2.

A duct 70 for connection to the bottle 13 forms a second path of the distributor. It comprises a hollow needle 72 protruding from the base 26. The needle 72 extends parallel to the elbowed portion 50C and is intended, like the latter, to penetrate into the bottle through the perforable protective cap 15. The bevelled ends of the needles 50 and 72 are arranged in proximity to each other and are preferably spaced by less than 1 cm and preferably by 1 to 3 mm.

The base 26 has a collar 74 surrounding the protruding end of the needle 72. The collar defines a space for receiving the neck of the bottle 13 and has profiles 76 for resilient engagement behind the neck in order to effect the mechanical connection of the bottle and the distributor.

The elbowed portion 50C extends in the space defined by the collar 74, the portion 50C and the needle 72 extending parallel to one another for the perforation of the protective cap 15.

The third path of the distributor comprises a duct for transfer to the perfusion bag 16. Said duct is equipped with a hollow needle 82 protruding from the base 26, in a generally cylindrical socket 84 provided in the base and suitable for receiving a tip 86 of the perfusion bag 16.

As is known per se, the tip 86 is generally cylindrical and is perforable to permit access to the bag through an access duct 88.

The protruding end of the needle 82 is covered over its entire length by a perforable resilient hood 90 in the form of a bellows suitable for being compressed axially along the needle 82.

The tap 64 is mounted to be rotatable about its axis, the latter extending perpendicularly to the plane in which the ducts 30, 70 and 80 extend.

A peripheral groove 92 is provided on the tap 64 to permit the selective connection of the ducts. The groove extends through 180°. Thus the tap is adapted such that, in a first position, termed transfer position, it effects the connection of the ducts 30 and 80, the duct 70 being closed and, in a second position, termed preparation position, it effects the connection of the ducts 30 and 70, the duct 80 being closed.

The reconstitution kit is used in the following manner.

Initially, the bag 16 and the bottle 13 are not connected to the syringe 12, as illustrated in FIG. 2. The syringe is stored in a sterile package.

Figure 3:
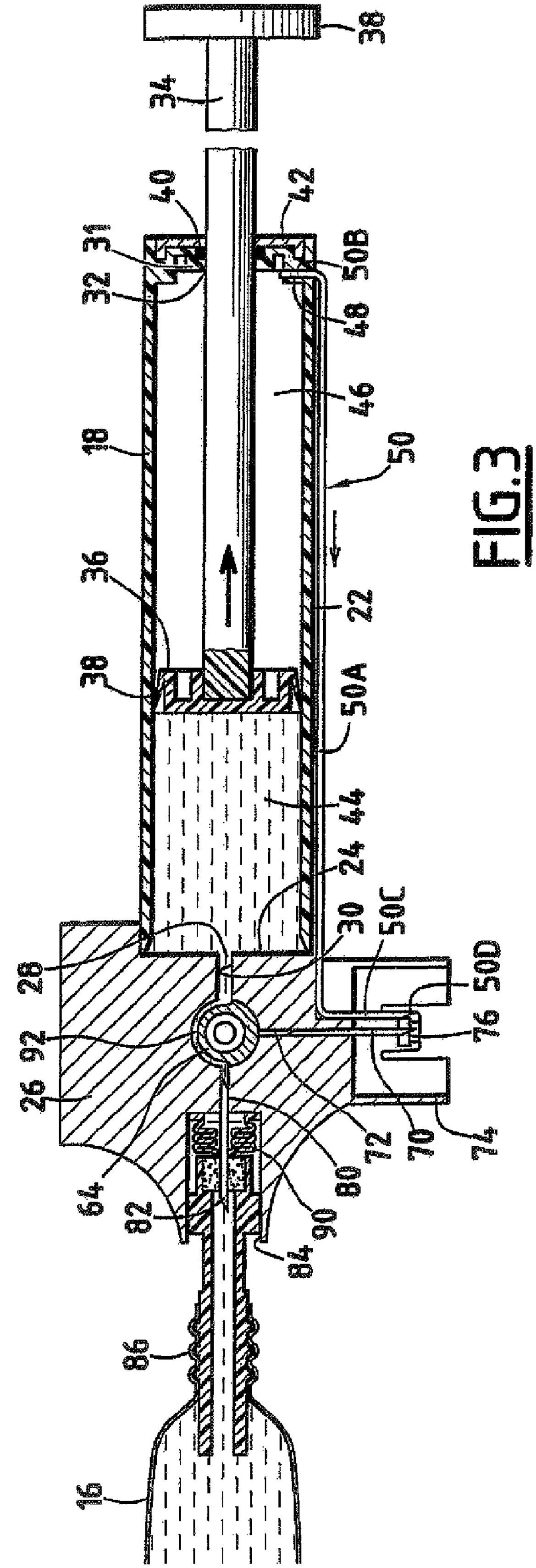

After being taken out of the package, the syringe 12 is first connected to the bag 16 via the needle 82. To this end, the tip 86 of the bag is engaged in the socket 84, so that the hood 90 is perforated by the needle 82 and retracts along said needle. The bevelled end of the needle 82 pierces the tip of the bag and thus comes into contact with the solvent contained in the bag, as illustrated in FIG. 3.

With the tap of the distributor in its transfer position and connecting the ducts 30 and 80, the piston 36, initially pressed against the front wall 24, is drawn towards the rear. By the action of the displacement of the piston 36, solvent is gradually drawn from the bag and is received in the containment chamber 44, as illustrated in FIG. 3. The air contained in the auxiliary chamber 46 is gradually evacuated via the auxiliary connection element 50. The air is expelled into the atmosphere, without any consequence, since the air is sterile.

After the chamber 44 is filled with a satisfactory amount of solvent, the bottle 13 is connected. To this end, the neck of the bottle is introduced into the space defined by the collar 74. The protective cap 15 is then perforated at the same time by the needle 72 and the needle 50.

The tap 64 is then turned through 90° in order to be brought into its preparation position, so that the ducts 30 and 70 are connected to each other, the duct 80 being isolated. In this position, the containment chamber 44 is connected to the bottle 13 via the needle 72, while the auxiliary return chamber 46 is also connected to the bottle 13 by the auxiliary connection element formed by the needle 50.

For correct operation, the bottle is placed with its neck facing upwards and, as illustrated in FIG. 4, the piston is then pushed forwards, leading to the expulsion of the solvent towards the inside of the bottle through, in succession, the ducts 30 and 70. Simultaneously, the excess gas contained in the bottle 13 is aspirated into the auxiliary return chamber 46 through the needle 50. The excess gas contained in the bottle is transferred to the return chamber by the combined action of the over-pressure arising in the bottle 13 and the aspirating action of the auxiliary chamber 46, owing to the displacement of the piston 36.

All the solvent contained in the containment chamber 44 is thus transferred to the bottle. The solvent then mixes with the powder constituting the cytotoxic active ingredient.

The bottle 13 is then turned over, so that the free end of the needle 72 is in contact with the mixture, as illustrated in FIG.

Figure 5:
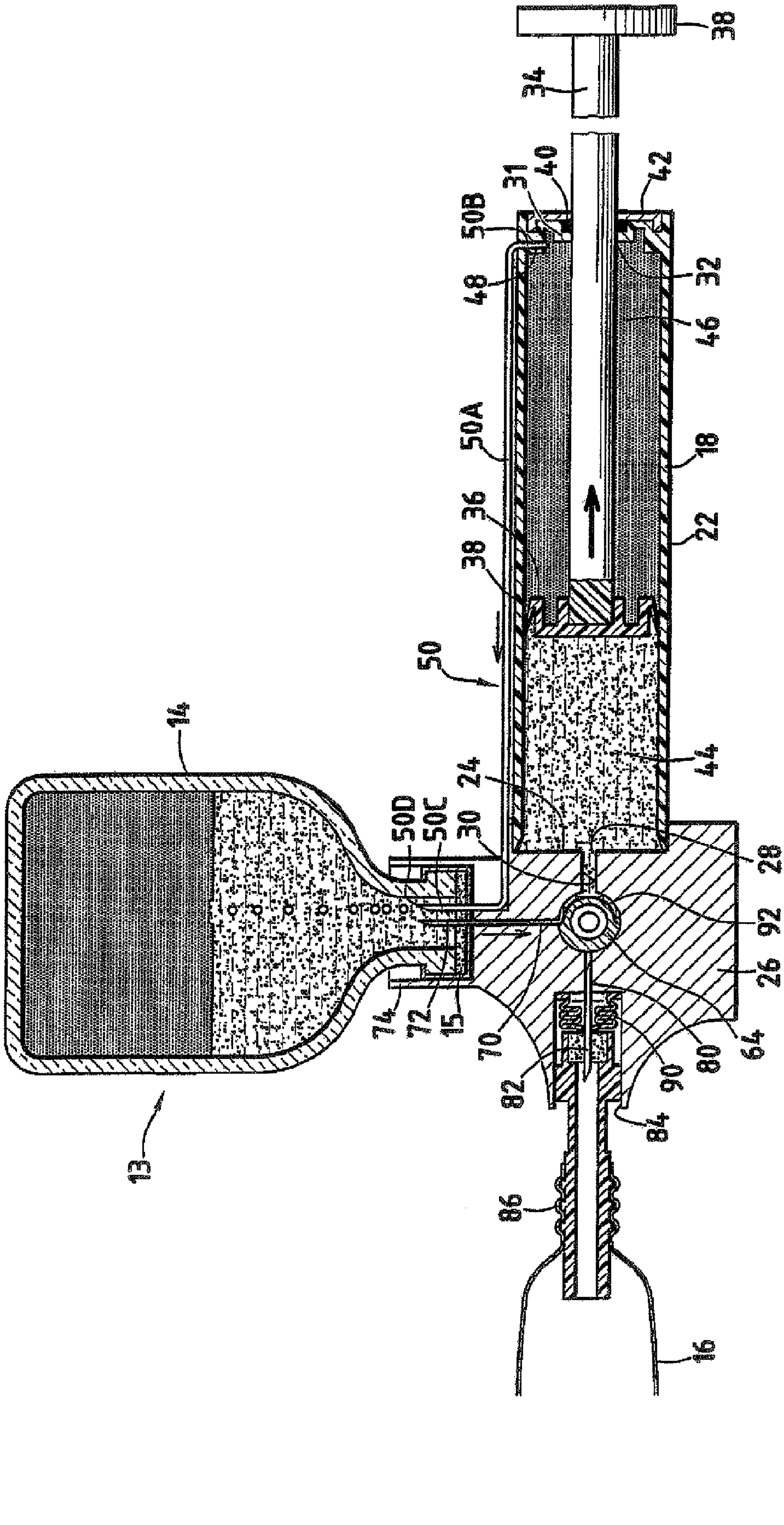

5. The piston 36 is then displaced towards the rear of the syringe body by pulling on the rod 34, as illustrated in FIG. 5. The mixture is thus re-aspirated into the containment chamber 44 through, in succession, the ducts 70 and 30.

Simultaneously, the gas previously aspirated into the auxiliary return chamber 46 is reintroduced into the bottle 13, to occupy the space left free by the mixture evacuated to the containment chamber 44.

Figure 6:
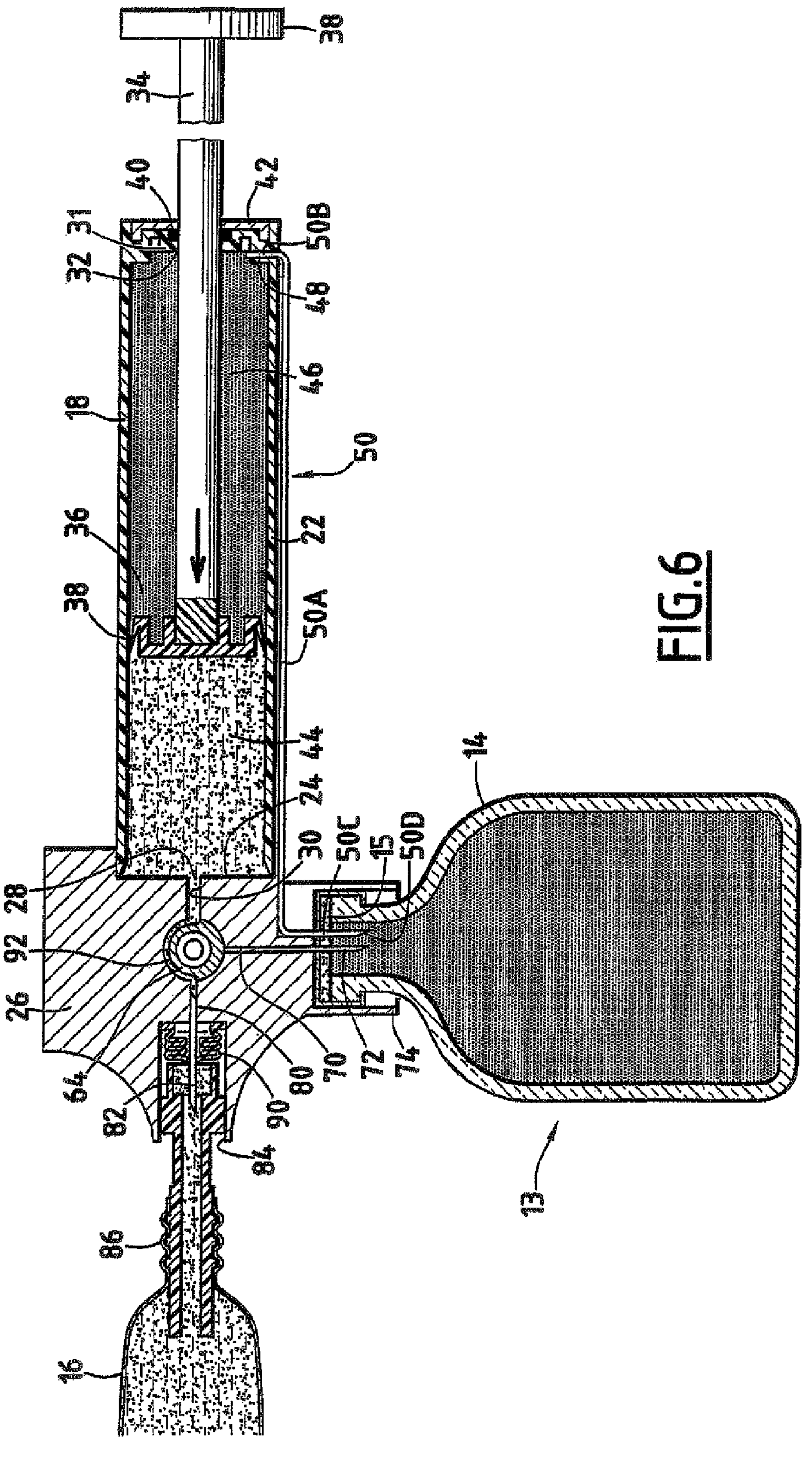

All the mixture is thus re-aspirated into the syringe. As illustrated in FIG. 6, the tap 64 is then brought into its transfer position, effecting the connection between the ducts 30 and 80. The mixture contained in the containment chamber 44 is then reintroduced into the bag 16 through, in succession, the ducts 30 and 80 by the action of the piston 36 pushed axially towards the front of the syringe body. During this transfer, the bottle 13 remains connected and gas drawn from the bottle is aspirated into the return chamber. Thus a slight under-pressure is produced in the bottle 13.

After the transfer of all the mixture contained in the containment chamber 44 or of a volume determined by means of the graduations of the syringe, the bag 16 is separated from the syringe by disengagement of the tip 86 from the socket 84. By the action of the resilience of the hood 90, the latter expands along the needle 82 to completely cover the end of same. Thus, the mixture still contained in the needle is confined inside the hood 90, avoiding any transfer of the mixture in liquid and gaseous form to the outside.

With such a device, no gaseous emission containing molecules of the cytotoxic active ingredient is released into the atmosphere. In fact, the gaseous emissions which may occur in the bottle during the reconstitution of the extemporaneous mixture during the different stages of use of the syringe are systematically confined in the bottle and/or in the auxiliary return chamber 46. Since the bottle 13 and the syringe 46 remain definitively connected, no contact occurs between the inside of the bottle and the chamber 46, and the outside.

It will be imagined that with such a device, the operator is protected against any pollution resulting from the use of the cytotoxic active ingredient.

The invention claimed is:

1. A syringe comprising:
   - a syringe body having a cylindrical wall extending along a longitudinal axis from one end of the body to another end and having a generally circular section closed at a forward end by a transverse wall in which a circulatory passage for the circulation of fluid is defined, said circulatory passage being extended by a main element for fluidic connection to a complementary volume, and
   - a movable piston inside the syringe body defining, with the cylindrical wall of the syringe body, a chamber for the containment of fluid, wherein the containment chamber opens out through said circulatory passage,
   - wherein the syringe body defines a closed space in which the piston is movably mounted, wherein the piston defines in the closed space, in addition to the fluid containment chamber, an auxiliary return chamber, the cylindrical wall of the syringe body comprising a return passage opening out into said auxiliary return chamber, and wherein said return passage is extended by an auxiliary element for connection to said complementary volume.

2. A syringe according to claim 1, wherein said auxiliary connection element comprises a hollow needle.

3. A syringe according to claim 1, wherein the syringe comprises a piston actuating rod connected to the piston and protruding out of the syringe body from a rearward end, said circulatory passage being formed at the forward end of the syringe body, and said return passage is formed in proximity to the rearward end of the cylindrical wall of the syringe body and the auxiliary connection element extends along the length of the syringe body from the return passage to the vicinity of the forward end.

4. A syringe according to claim 1, wherein the main element for fluidic connection includes a distributor comprising a base defining at least three paths for circulation and a closure means movable in relation to the base, a first path being connected to said circulatory passage, a second path comprising a duct for connection to said complementary volume and a third path comprising a transfer duct, said closure means being movable between a transfer position in which the first and third paths are connected, and a preparation position in which the first and second paths are connected.

5. A syringe according to claim 4, wherein the syringe body and the distributor are inseparable.

6. A syringe according to claim 4, wherein the transfer duct comprises a hollow needle.

7. A syringe according to claim 6, wherein said hollow needle of the transfer duct has a perforable and resiliently deformable hood covering the hollow needle.

8. A syringe according to claim 4, wherein the connecting duct comprises a hollow needle and wherein said auxiliary connection element comprises a hollow needle.

9. A syringe according to claim 8 taken together, wherein the free end portions of the hollow needles of the auxiliary connection element and of the connecting duct are spaced by less than 1 cm.

10. A reconstitution kit comprising a syringe according to claim 1, and a complementary volume suitable for simultaneous connection to the containment chamber and the auxiliary return chamber respectively via the main element for fluidic connection and the auxiliary connection element, so that, when the fluid containment chamber is connected to the complementary volume via the main element, and the auxiliary chamber is connected to the same complementary volume via the auxiliary element, and when moving the piston, a solvent initially contained in the containment chamber is expelled toward the complementary volume through the circulatory passage, and an excess gas contained in the complementary volume is aspirated into the auxiliary chamber through the return passage.

* * * * *